United States Patent
Liu et al.

(10) Patent No.: US 9,066,998 B2
(45) Date of Patent: Jun. 30, 2015

(54) DEVICES AND METHOD FOR TISSUE ENGINEERING

(75) Inventors: James Jenq Liu, Mason, OH (US); Casey S. Lewis, Medford, MA (US)

(73) Assignee: BIO2 TECHNOLOGIES, INC., Woburn, MA (US)

( * ) Notice: Subject to any disclaimer, the term of this patent is extended or adjusted under 35 U.S.C. 154(b) by 596 days.

(21) Appl. No.: 13/410,458

(22) Filed: Mar. 2, 2012

(65) Prior Publication Data

US 2013/0228947 A1    Sep. 5, 2013

(51) Int. Cl.
  *B29C 65/00* (2006.01)
  *A61L 27/10* (2006.01)
  *A61L 27/56* (2006.01)

(52) U.S. Cl.
  CPC *A61L 27/56* (2013.01); *A61L 27/10* (2013.01)

(58) Field of Classification Search
  USPC .............. 264/41–44, 45.1, 45.5, 48, 413, 414
  See application file for complete search history.

(56) References Cited

U.S. PATENT DOCUMENTS

| | | | |
|---|---|---|---|
| 2004/0262801 A1* | 12/2004 | Hojaji et al. | 264/44 |
| 2010/0180724 A1* | 7/2010 | Grohowski, Jr. | 75/228 |
| 2011/0104231 A1 | 5/2011 | Dunkley et al. | |
| 2011/0106272 A1 | 5/2011 | Liu | |
| 2011/0195838 A1 | 8/2011 | Brady et al. | |
| 2011/0206828 A1 | 8/2011 | Liu et al. | |

OTHER PUBLICATIONS

Rahaman, M N., et al., "Bioactive Glass in Tissue Engineering", *Acta Biomaterialia*, vol. 7(6), (Jun. 2011),2355-2373.

* cited by examiner

*Primary Examiner* — Stella Yi

(57) ABSTRACT

A method of fabricating a bioactive porous tissue scaffold is herein provided. Bioactive materials having a composition of biologically active materials that define a group of surface reactive glass, glass-ceramic, and ceramic materials that most commonly include a range of silicate, borate, and phosphate-based glass systems. These materials typically exhibit a narrow working range that require heating methods that use pore former combustion to control thermal variations during processing.

6 Claims, 2 Drawing Sheets

DEVICES AND METHOD FOR TISSUE ENGINEERING

FIELD OF THE INVENTION

The present invention relates generally to the field of medical devices and implants. More specifically, the invention relates to a method of fabricating a bioactive implant having osteostimulative properties in vivo.

BACKGROUND OF THE INVENTION

Prosthetic devices are often required for repairing defects in bone tissue in surgical and orthopedic procedures. Prostheses are increasingly required for the replacement or repair of diseased or deteriorated bone tissue in an aging population and to enhance the body's own mechanism to produce rapid healing of musculoskeletal injuries resulting from severe trauma or degenerative disease.

Tissue engineering scaffolds as prostheses for the replacement and repair of bone tissue promote ingrowth of bone tissue in the body's natural healing process when the physical characteristics of the scaffold material are biocompatible and osteostimulative. The ingrown tissue and the tissue surrounding the implantation site becomes healthy and mature when the mechanical properties of the scaffold material are closely matched to the mechanical properties of the surrounding tissue, i.e., natural bone material. Various materials have been developed for prosthetic devices in an attempt to provide a material with the physical characteristics and mechanical properties of natural bone materials. These materials have been developed in various compositions and composites that attain at least a portion of the desired characteristics, but nearly all materials compromise an aspect of the requirements of an ideal tissue engineering scaffold.

BRIEF SUMMARY OF THE INVENTION

The present invention meets the objectives of providing a porous bioactive medical implant or device.

According to an embodiment of the present invention a method is provided to form a porous tissue scaffold. The method includes the steps of mixing bioactive material in fiber and/or particulate form, the bioactive material having a discrete size distribution, with a first pore former and a second pore former. Binder and a liquid are included to provide a green mixture that can be formed or shaped into a desired configuration. The shaped object is dried and the binder is next removed. The formed object is then heated to the ignition temperature of the first pore former so that the first pore former combustion can be used to internally heat the formed object. The formed object is then heated to the ignition temperature of the second pore former so that the second pore former combustion can be used to internally heat the formed object. The cooperative heating of the formed object by the combustion of the first pore former and the second pore former is a heat source to raise the temperature of the formed object so that the bioactive material creates a porous tissue scaffold.

BRIEF DESCRIPTION OF THE SEVERAL VIEWS OF THE DRAWINGS

The foregoing and other objects, features, and advantages of the invention will be apparent from the following detailed description of the several embodiments of the invention as illustrated in the accompanying drawings in which like reference characters refer to the same parts throughout the different views. The drawings are not necessarily to scale, with emphasis instead being placed upon illustrating the principles of the invention.

Figure 1:
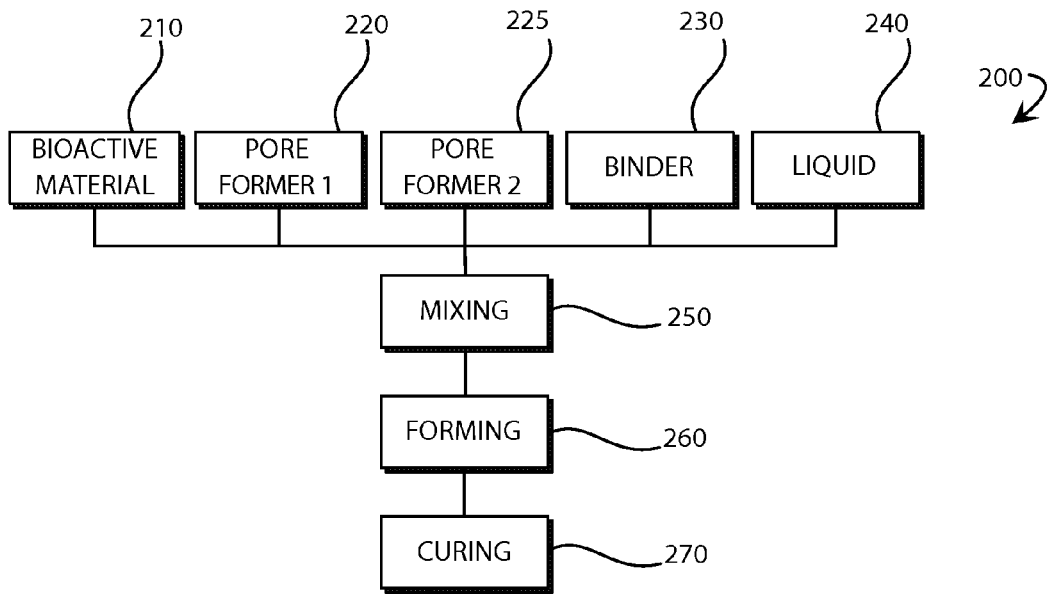
FIG. 1 depicts a flowchart of the present invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

The present invention provides a tissue engineering scaffold for the repair of tissue defects. Various types of synthetic implants have been developed for tissue engineering applications in an attempt to provide a synthetic prosthetic device that promotes tissue ingrowth and the growth of healthy bone tissue. These synthetic implants are typically composed of a biocompatible material with a specific microstructure provides a temporary support for tissue cells to guide their proliferation and integration into the surrounding tissue.

Devices when implanted into living tissue evoke a biological response dependent upon a number of factors, such as the composition of the implant. Biologically inactive materials are commonly encapsulated with fibrous tissue to isolate the implant from the host. Metals and most polymers produce this interfacial response, as do nearly inert ceramics, such as alumina or zirconia. Biologically active materials or bioactive materials, elicit a biological response that can produce an interfacial bond securing the implant material to the living tissue, much like the interface that is formed when natural tissue repairs itself. This interfacial bonding can lead to an interface that stabilizes the scaffold or implant in the bony bed and provide stress transfer from the scaffold across the bonded interface into the bone tissue. When loads are applied to the repair, the bone tissue including the regenerated bone tissue is stressed, thus limiting bone tissue resorption due to stress shielding. A bioresorbable material can elicit the same response as a bioactive material, but can also exhibit complete chemical degradation by body fluid.

Bioactive materials as used herein include a group of surface reactive glass, glass-ceramic and ceramic materials that most commonly include a range of silicate, borate, and phosphate-based glass or glass-ceramic systems. Compositions of various bioactive glass materials include those listed in Table 1.

TABLE 1

Compositions of Bioactive Glass Materials

| (wt %) | 45S5 | 13-93 | 6P53B | 58S | 70S30C | 13-93B1 | 13-93B3 | $P_{50}C_{35}N_{15}$ |
|---|---|---|---|---|---|---|---|---|
| $Na_2O$ | 24.5 | 6.0 | 10.3 | 0 | 0 | 5.8 | 5.5 | 9.3 |
| $K_2O$ | 0 | 12.0 | 2.8 | 0 | 0 | 11.7 | 11.1 | 0 |
| MgO | 0 | 5.0 | 10.2 | 0 | 0 | 4.9 | 4.6 | 0 |
| CaO | 24.5 | 20.0 | 18.0 | 32.6 | 28.6 | 19.5 | 18.5 | 19.7 |
| $SiO_2$ | 45.0 | 53.0 | 52.7 | 58.2 | 71.4 | 43.4 | 0 | 0 |
| $P_2O_5$ | 6.0 | 4.0 | 6.0 | 9.2 | 0 | 3.8 | 3.7 | 71.0 |
| $B_2O_3$ | 0 | 0 | 0 | 0 | 0 | 19.9 | 56.6 | 0 |

Bioactive materials, including the glass systems in the compositions listed in Table 1 and others including variations thereto have been shown to enhance the formation of new bone in vivo. The biochemical mechanism of bioactivity and bone formation of bioactive materials have been widely studied. Without wishing to be bound by theory, it is believed that a carbonate-substituted hydroxyapatite layer that forms on the surface in contact with the body fluid is the basis for bioactive material bonding to living tissue. Because the hydroxyapatite layer is compositionally similar to the that of bone it very quickly bonds to bone through ion exchange once the layer forms in vivo.

Furthermore, the bioactivity of these compositions results in resorption when implanted in vivo. When implanted the bioactive material chemically degrades releasing sodium and/or calcium ions as the hydroxyapatite-like material precipitates. Silicon and/or phosphate and/or boron oxides are released during this chemical degradation by dissolution and/or by other mechanisms that is harmlessly excreted from the body in soluble form through urine.

Tissue scaffold materials having a porous microstructure can provide tissue ingrowth to promote healing broken, diseased or malformed bone tissue when implanted in vivo. It is generally known that the porous scaffold material should approximate the mechanical properties of the surrounding bone tissue, such as tensile and compressive strength and elastic modulus to promote the ingrowth of healthy tissue. A porous tissue scaffold in a bioactive material composition is particularly desirable as it promotes tissue ingrowth as it chemically degrades through resorption, resulting in the replacement of living tissue through remodeling.

Porous bioactive scaffolds are commonly prepared by heating or sintering particles of bioactive materials into a formed shape to bond the particles into a cohesive phase of bioactive materials containing an interconnected network of pores. A limitation of bioactive glass materials, however, is its limited ability to sinter by viscous flow above its glass transition temperature and its inherently narrow working range (i.e., the range of temperature between the glass transition and devitrification temperature, upon which crystallization occurs). Devitrification of the bioactive glass material does not necessarily reduce or disable its bioactive nature.

Silicate bioactive glass materials are based on soda-lime glass (derived from oxides of sodium, calcium, and silica) having a relatively low silica content with high glass network modifier content to exhibit bioactivity. Borate bioactive glass compositions are typically less chemically durable and thus, exhibit increased rates of degradation and resorption. Borate bioactive glass materials exhibit bioactivity and promote bone formation in a mechanism similar to silica-based bioactive materials. Phosphate bioactive glass compositions are based on $P_2O_5$ glass forming network with CaO and $Na_2O$ as modifiers. The constituents to phosphate bioactive glass materials are present in the composition of natural bone and thus, the material exhibits an affinity with bone. Bioactive glass-ceramic materials and bioactive ceramic materials are typically derived from heat treatment of glass materials. For example, beta-wollastonite is a calcium silicate crystalline phase in a magnesia calcium silicate glass that exhibits high levels of bioactivity which can be derived from heat treatment of a magnesia calcium silicate glass. Similarly, apatite-wollastonite is a bioactive ceramic material that can be derived from heat treatment of a magnesia calcium silicate phosphate glass.

Bioactive material porous tissue scaffolds for orthopedic applications are most commonly fabricated from particles of glass, glass-ceramic, or ceramic materials that are prepared from melt-derived glass and/or heat treated glass materials. Typically, the bioactive material composition is prepared from a conventional glass or ceramic processing techniques that is converted into particles such as a powder or fiber form that is then prepared into the orthopedic implant or device by sintering the glass particles into a formed object. Preparation of the particle-sized bioactive material composition can alternatively be performed using other known glass preparation methods and techniques, including, for example, electrospinning of a solution or a viscous melt-drawn fiber, or sol-gel processing.

The use of pore formers to influence and/or define the pore size distribution in a porous tissue scaffold of bioactive glass is described in commonly assigned and co-pending U.S. patent application Ser. Nos. 12/832,391 and 12/832,394, both filed Jul. 8, 2010, and both herein incorporated by reference. Because of the narrow working range of bioactive glass materials, as described above, and the inherent thermal sensitivity of bioactive glass-ceramic and ceramic materials, the method of the present invention uses combustion of the pore former to heat the bioactive material to control the heating rate and temperature. Referring to FIG. 1 an embodiment of the method 200 of the present invention is shown. Generally, bioactive material 210 having a discrete size distribution is mixed with a binder 230, a plurality of pore formers including at least a first pore former 220 and a second pore former 225, and a liquid 240, which is then cured into a porous body. The curing step removes the binder and pore formers while fusing and bonding the bioactive material into a porous structure. The first pore former 220 and the second pore former 225 collectively contribute to the pore size distribution within the porous structure and provide a controlled heating mechanism to increase the temperature of the bioactive material within the working range of the bioactive material to prevent encapsulation and/or contamination of the resulting scaffold with residual raw material components.

According to the method of the present invention, the bioactive material 210 has a discrete size distribution that determines the natural packing density of the material. If the discrete size distribution of the bioactive material 210 is a single mode with a narrow distribution of small particles, for example, 0.50 μm to 0.75 μm, the bioactive material 210 can form a relatively dense material and high relative quantities of pore former, including the first pore former 220 and the second pore former 225 may be necessary to provide porosity greater than 50% in the porous structure. Conversely, if the discrete size distribution of the bioactive material 210 is a single mode with a narrow distribution of large particles, for example, 20 μm to 50 μm, the bioactive material 210 can form an inherently porous material with low relative quantities of pore former, including the first pore former 220 and the second pore former 225 to provide porosity greater than 50% in the porous structure.

The bioactive material 210 may exhibit multiple modes of discrete size distributions with modes indicating fine powders less than 1.0 μm, small particles 1 μm-20 μm, medium particles 20 μm-100 μm and large particles 100 μm and above. The bioactive material 210 can be particles having an aspect ratio of approximately 1 (length to width). The bioactive material 210 can be particles having extended lengths relative to the particle width (i.e., aspect ratio greater than 1). Alternatively, the bioactive material 210 can be in a fiber form wherein the discrete size distribution is related to the fiber diameter, the fiber length, and/or the aspect ratio of the fiber (length to diameter). Additionally, the bioactive material 210 can be a mixture of fiber and particle-based material where the discrete size distribution can have a mode of fine, small, medium or large particles with a mode of a specific fiber diameter, length, or aspect ratio.

The bioactive material 210 in fiber form can be provided in bulk form, continuous form, or as chopped fibers. The diameter of the fiber can range from about 1 to about 200 μm and typically between about 5 to about 100 μm. Bioactive material 210 in fiber form is typically produced with a relatively narrow and controlled distribution of fiber diameter and fiber of a specific diameter may be used or a mixture of fibers having a range of fiber diameters can be used. The discrete size distribution of the bioactive material 210 in fiber form can relate to the fiber length. Bioactive material 210 in fiber form having a diameter in the typical range from about 1 to about 200 μm can be provided chopped in lengths that are 1 to 1,000 times the diameter.

The bioactive material 210 can be a specific composition including silica bioactive glass, borate bioactive glass, or phosphate bioactive glass and a composite of different compositions or variations of glass, glass-ceramic and ceramic bioactive materials. Similarly, the bioactive material 210 can include compositions that may fall outside the compositional range of bioactivity that when heat treated during the curing step 270, when reacting with other constituents in the bioactive material 210 converts to a composition that exhibits bioactivity.

The plurality of pore formers including at least the first pore former 220 and the second pore former 225 enhance the pore space of the resulting tissue scaffold. Pore formers are non-reactive materials that occupy volume in the green mixture that influence and define the size, shape, and interconnectivity of the resulting porosity. Pore formers including the first pore former 220 and the second pore former 225 can typically range between about 25 μm or less to about 450 μm or more. The pore formers must be readily removable during the curing step 270 without significantly disrupting the relative position of the bioactive material 210 that surrounds the pore former. The pore formers, including the first pore former 220 and the second pore former 225, and any additional pore formers comprising the plurality of pore formers, are not miscible or dissolvable in the liquid 240 as the relative shape, size, and spatial distribution of the plurality of pore formers is necessary to control the pore size distribution in the porous structure.

The binder 230 and the liquid 240, when mixed with the bioactive material 210 and the first pore former 220 and the second pore former 225, create a plastically formable batch mixture that enables the bioactive material 210 to be evenly distributed throughout the batch mixture to be formed in the desired shape in the subsequent forming step 260. An organic binder material can be used as the binder 230, such as methylcellulose, hydroxypropyl methylcellulose (HPMC), ethylcellulose and combinations thereof. The binder 230 can include materials such as polyethylene, polypropylene, polybutene, polystyrene, polyvinyl acetate, polyester, isotactic polypropylene, atactic polypropylene, polysulphone, polyacetal polymers, polymethyl methacrylate, fumaron-indane copolymer, ethylene vinyl acetate copolymer, styrene-butadiene copolymer, acryl rubber, polyvinyl butyral, inomer resin, epoxy resin, nylon, phenol formaldehyde, phenol furfural, paraffin wax, wax emulsions, microcrystalline wax, celluloses, dextrines, chlorinated hydrocarbons, refined alginates, starches, gelatins, lignins, rubbers, acrylics, bitumens, casein, gums, albumins, proteins, glycols, hydroxyethyl cellulose, sodium carboxymethyl cellulose, polyvinyl alcohol, polyvinyl pyrrolidone, polyethylene oxide, polyacrylamides, polyethyterimine, agar, agarose, molasses, dextrines, starch, lignosulfonates, lignin liquor, sodium alginate, gum arabic, xanthan gum, gum tragacanth, gum karaya, locust bean gum, irish moss, scleroglucan, and cationic galactomanan, or combinations thereof. Although several binders 230 are listed above, it will be appreciated that other binders may be used. The binder 230 provides the desired rheology of the plastic batch material in order to form a desired object while remaining inert with respect to the bioactive material 210 and the first pore former 220 and the second pore former 225. The binder 230 preferably is miscible with the liquid 240 and is capable of thermal disintegration or selective dissolution, without impacting the chemical composition of the bioactive material 210 or the pore formers.

The liquid 240 is added as needed to attain a desired rheology in the plastic batch material suitable for forming the plastic batch material into the desired object in the subsequent forming step 260. Water is typically used, though solvents of various types can be utilized. Rheological measurements can be made during the mixing step 250 to evaluate the plasticity and cohesive strength of the mixture prior to the forming step 260.

The relative quantities of the respective materials, including the bioactive material 210, the first pore former 220 and the second pore former 225, the binder 230, and the liquid 240 depend on the overall porosity desired in the bioactive tissue scaffold 100. For example, to provide a porous tissue scaffold having approximately 60% porosity, bioactive material 210 would amount to approximately 40% of the mixture by volume. The relative quantity of volatile components, such as the first pore former 220 and the second pore former 225, the binder 230 and the liquid 240 would amount to approximately 60% of the mixture by volume, with the relative quantity of binder to liquid determined by the desired rheology of the mixture. It can be appreciated that the relative quantities of the bioactive material 210 and the remaining components and the resulting porosity of the scaffold 100 will vary as the material density may vary due to the reaction of the components during the curing step 270. Specific examples are provided herein below.

In the mixing step 250, the bioactive material 210, the first pore former 220 and the second pore former 225, the binder 230, and the liquid 240 are mixed into a homogeneous mass of a plastically deformable and uniform mixture. The mixing step 250 may include dry mixing, wet mixing, shear mixing, and kneading, which can be necessary to evenly distribute the material into a homogeneous mass while imparting the requisite shear forces to break up and distribute or de-agglomerate the raw materials. The amount of mixing, shearing, and kneading, and duration of such mixing processes depends on the selection of materials, along with the selection of the type of mixing equipment used during the mixing step 250, in order to obtain a uniform and consistent distribution of the materials within the mixture, with the desired rheological properties for forming the object in the subsequent forming step 260. Mixing can be performed using industrial mixing equipment, such as batch mixers, shear mixers, and/or kneaders.

The forming step 260 forms the mixture from the mixing step 250 into the object that will become the porous material. The forming step 260 can include extrusion, rolling, pressure casting, or shaping into nearly any desired form in order to provide a roughly shaped object that can be cured in the curing step 270 to provide the porous material. It can be appreciated that the final dimensions of the porous material may be different than the formed object at the forming step 260, due to expected shrinkage of the object during the curing step 270, and further machining and final shaping may be necessary to meet specified dimensional requirements. In an exemplary embodiment to provide samples for mechanical and in vitro and in vivo testing, the forming step 260 extrudes the mixture into a cylindrical rod using a piston extruder forcing the mixture through a round die.

Figure 2:
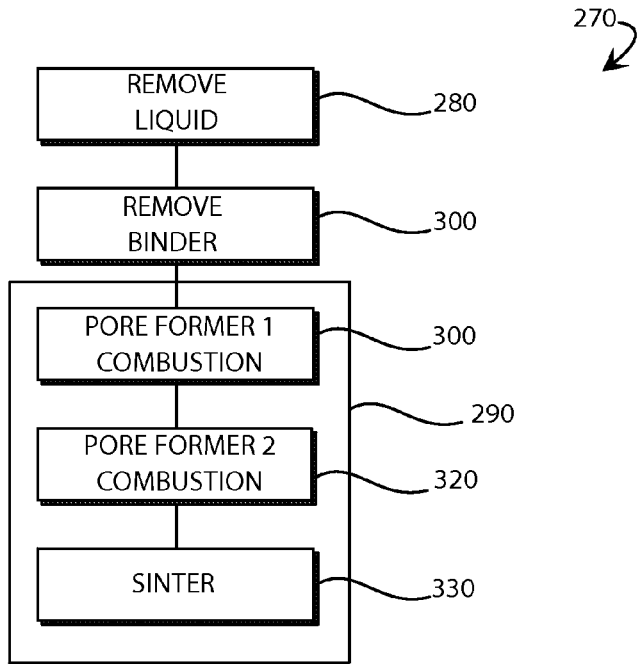
FIG. 2 depicts a flowchart of the curing step of the method according to FIG. 1.

The curing step 270 is shown in more detail in FIG. 2. The curing step 270 can be performed as the sequence of three phases: a drying step to remove the liquid 240; a binder removal step 300; and a bond formation step 290. In the first phase, the remove liquid (or drying) step 280, the formed object is dried by removing the liquid using slightly elevated temperature heating with or without forced convection to gradually remove the liquid. Various methods of heating the object can be used, including, but not limited to, heated air convection heating, vacuum freeze drying, solvent extraction, microwave or electromagnetic/radio frequency (RF) drying methods. The liquid within the formed object is preferably not removed too rapidly to avoid drying cracks due to shrinkage. Typically, for aqueous based systems, the formed object can be dried when exposed to temperatures between about 90° C. and about 150° C. for a period of about one hour, though the actual drying time may vary due to the size and shape of the object, with larger, more massive objects taking longer to dry. In the case of microwave or RF energy drying, the liquid itself, and/or other components of the object, adsorb the radiated energy to more evenly generate heat throughout the material. During the remove liquid step 280, depending on the selection of materials used as the volatile components, the binder 230 can congeal or gel to provide greater green strength to provide rigidity and strength in the object for subsequent handling. The remove liquid step 280 can be performed in a low temperature drying oven separate from the subsequent heating steps, or all three of the phases can be performed in the same kiln or oven.

Once the object is dried, or substantially free of the liquid component 240 by virtue of the remove liquid step 280, the next phase of the curing step 270 proceeds to the binder removal step 300. Here, the binder material is thermally decomposed by heating the formed object to a temperature sufficient to thermally degrade and volatilize the binder 230 while at a temperature below which the remaining components react. For example, HPMC used as a binder 230 will thermally decompose at temperatures between about 260-300° C.

As referenced above, the first pore former 220 and the second pore former 225 cooperatively heat the bioactive material 210 to a temperature within the working range of the material to minimize thermal gradients throughout the formed object during the bond formation step 290. The first pore former 220 is selected to have an ignition temperature that is less than the ignition temperature of the second pore former 225. In this way, as the formed object is heated during the bond formation step 290, when the ignition temperature of the first pore former 220 is attained, the first pore former 220 begins to combust to contribute and accelerate the heating rate of the formed object to attain the ignition temperature of the second pore former 225. In this way, the combustion of the first pore former 220 effectively operates to assist in the ignition of the combustion of the second pore former with a minimal thermal gradient throughout the formed object.

Figure 3:
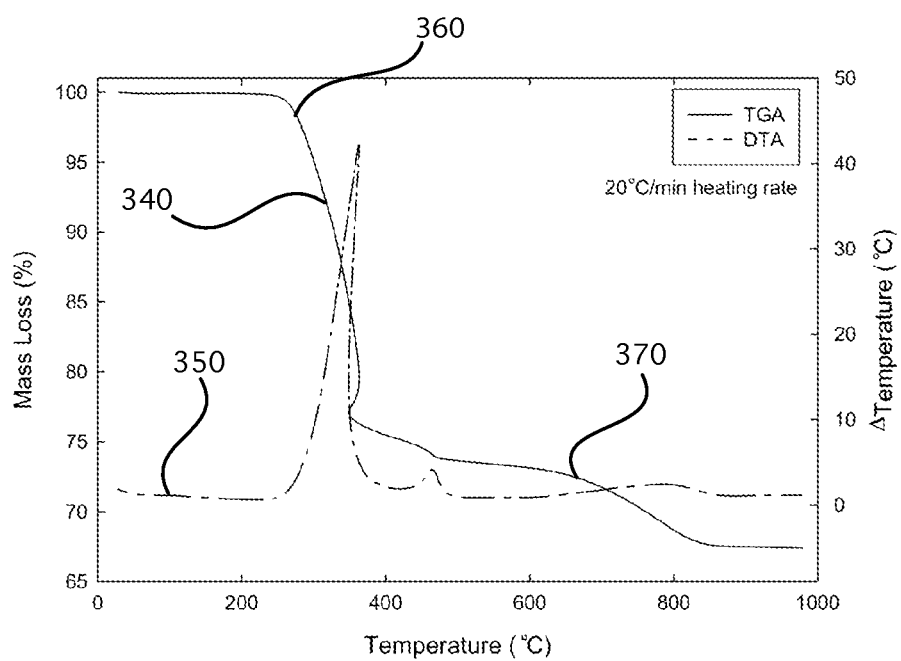
FIG. 3 shows a ThermoGravimetric Analysis (TGA)/Differential Thermal Analysis (DTA) of an illustrative embodiment of the present invention.

FIG. 3 depicts a ThermoGravimetric Analysis (TGA)/Differential Thermal Analysis (DTA) of an illustrative embodiment of the present invention to simulate the heating mechanism of the combustion of the first pore former 220 and the second pore former 225 during the bond formation step 290. The illustrative embodiment was fabricated using the first pore former 220 provided as polymethyl methacrylate (PMMA) having an ignition temperature of about 350° C. The second pore former 225 is graphite particles having an ignition temperature of about 650° C. As shown in FIG. 3 the thermogravimetric line 340 has a first inflection 360 that indicates a reduction in mass at the ignition temperature of the PMMA particles and a second inflection 370 of a reduction in mass at the ignition temperature of the graphite particles. The differential temperature line 350 exhibits temperature rates of change that correspond to the first inflection point 360 and the second inflection point 370.

The particle size and shape of the first pore former 220 and the second pore former 225 influence the resulting pore size and pore size distribution of the pore space of the porous tissue scaffold. Particle sizes of the first pore former 220 and the second pore former 225 can typically range between 5 μm or less to about 450 μm or more, or alternatively, the particle size for the first pore former 220 and the second pore former 225 can be a function of the discrete particle size distribution of the bioactive material 210 (e.g., the particle size of the first pore former 220 and the second pore former 225 can range from about 0.1 to about 100 times of a mode of the discrete size distribution of the bioactive material 210). According to the method of the present invention, the first pore former 220 and the second pore former 225 must be readily removable during the bond formation step 290 without significantly disrupting the relative position of the bioactive material 210.

Pore formers suitable for at least one of the first pore former 220 and the second pore former 225 include carbon particles, microwax emulsions, phenolic resin particles, carbon black, activated carbon, graphite flakes, synthetic graphite, wood flour, celluloses, coconut shell husks, latex spheres, bird seeds, saw dust, pyrolyzable polymers, polyalkyl methacrylate, polymethyl methacrylate, polyethyl methacrylate, poly n-butyl methacrylate, polyethers, poly tetrahydrofuran, poly (1,3-dioxolane), poly(alkalene oxides), polyethylene oxide, polypropylene oxide, methacrylate copolymers, polyisobutylene, polytrimethylene carbonate, poly ethylene oxalate, poly beta-propiolactone, poly delta-valerolactone, polyethylene carbonate, polypropylene carbonate, vinyl toluene/alpha-methylstyrene copolymer, styrene/alpha-methyl styrene copolymers, and olefin-sulfur dioxide copolymers. Although several materials are listed above that can be suitable for use as at least one of the first pore former 220 and the second pore former 225, it must be appreciated that other materials may be used as well where the ignition temperature of the material selected for the first pore former 220 is lower than the ignition temperature of the second pore former 225 so that complete combustion of the two materials can be attained during the bond formation step 290.

Referring back to FIG. 2, the bond formation step 290 is the combination of the combustion of the first pore former 300, the combustion of the second pore former 320, and the sintering step 330. The bond formation step 290 is performed in a heated environment that is adapted to increase the temperature of the formed object to initiate ignition of the first pore former 220 at step 300. It may be necessary to provide airflow into the heating environment in a controlled manner to regulate and/or support combustion of the first pore former 220 and the second pore former 225. The temperature of the formed object will increase uniformly during the combustion of the first pore former at step 300 so that the temperature of the formed object can be uniformly increased to the ignition temperature of the second pore former 225 to initiate combustion of the second pore former at step 320.

The final step of the bond formation step 290 is to sinter the bioactive material 210 into the porous tissue scaffold. At this final step the time and temperature required for additional heating to increase the temperature of the formed object to a temperature sufficient to sinter the bioactive material depends upon the bioactive material composition and the selection and relative quantity of the pore formers. For example, in the illustrative embodiment described above with a PMMA material for the first pore former 220 and graphite particles for the second pore former 225 where the ignition temperature for the first pore former 220 can be attained at approximately 350° C. and the ignition temperature for the second pore former 225 can be attained at approximately 600° C., the temperature rise of the formed object when heated by the combustion of the pore formers can attain the temperature sufficient to sinter bioactive glass in the 13-93 composition into a porous tissue scaffold.

The sintering step 330 of the bond formation step 290 is the phase upon which bonds are formed between the particles and/or fibers of the bioactive material 210 to create the porous tissue scaffold. Sintering is generally known as a method of diffusion bonding of particles that does not necessarily exclude melting or softening of the materials being bonded. As used herein the temperature upon which a bioactive composition can be sintered typically falls within a wide range that may attain or even exceed the glass transition temperature such that localized melting or softening of the glass material may be observed. Ignition and combustion of the pore former during the bond formation step 290 provides out-gassing of the combustion byproducts that can generate pores and define the resulting pore size distribution, thus impacting the effective permeability of the porosity of the scaffold. The sintering temperature for bioactive material compositions can influence the resulting strength and other mechanical and physical properties of the resulting porous tissue scaffold. Without the use of both a first pore former combustion step 300 and a second pore former combustion step 320 the temperature variations exhibited in a formed object of bioactive material with a single pore former may result in retention and encapsulation of pore former materials that can be released into the body during resorption of the bioactive material when implanted as a medical device or implant.

EXAMPLES

The following examples are provided to further illustrate and to facilitate the understanding of the disclosure. These specific examples are intended to be illustrative of the disclosure and not intended to be limiting in any way.

In a first exemplary embodiment a porous tissue scaffold is formed from 13-93 glass by mixing 22.5 grams of 13-93 glass particles having a particle size distribution with an average particle size of approximately 30 µm with 2.5 grams HPMC as the binder with 7.5 grams PMMA with a particle size of about 200 µm as the first pore former having an ignition temperature of approximately 350° C. and 2.5 grams graphite powder with a particle size ranging between 40-100 µm as the second pore former having an ignition temperature of approximately 600° C. and approximately 12 ml deionized water, adjusted as necessary to provide a plastically formable mixture. The mixture was formed into a 10 mm diameter rod and dried in a convection oven at 90° C. The dried part was then heated in an air-purged oven at 280° C. for 2 hours to remove the HPMC and then heated to a sintering temperature of 900° C. at a rate of 10° C. per minute holding for 30 minutes to sinter the porous tissue scaffold. In this example the tissue scaffold was measured to have 60% porosity In a second exemplary embodiment a porous tissue scaffold is formed from 13-93 glass by mixing 20 grams of 13-93 glass fiber having a diameter of 30 µm and chopped to a length of approximately 100 µm and 2.5 grams 13-93 glass ground into a powder with 5 grams HPMC as the binder with 2.5 grams polyethylene particles with a particle size of about 400 µm as the first pore former having an ignition temperature of approximately 350° C. and 2.5 grams graphite powder with a particle size ranging between 40-100 µm as the second pore former having an ignition temperature of approximately 600° C. and approximately 15 ml deionized water, adjusted as necessary to provide a plastically formable mixture. The mixture was formed into a 10 mm diameter rod and dried in a convection oven at 90° C. The dried part was then heated in an air-purged oven at 280° C. for 2 hours to remove the HPMC and then heated to a sintering temperature of 850° C. at a rate of 10° C. per minute holding for 3 hours to sinter the porous tissue scaffold. The porosity of this sample was measured to be 52.9%.

In a third exemplary embodiment a porous tissue scaffold is formed from 13-93 glass by mixing 22.5 grams of 13-93 glass fiber having a diameter of 30 µm and chopped to a length of approximately 100 µm with 5 grams HPMC as the binder with 5 grams PMMA with a particle size of about 200 µm as the first pore former having an ignition temperature of approximately 350° C. and 2.5 grams cellulose fiber with a particle size ranging between 70-140 µm as the second pore former having an ignition temperature of approximately 450° C. and approximately 13 ml deionized water, adjusted as necessary to provide a plastically formable mixture. The mixture was formed into a 10 mm diameter rod and dried in a convection oven at 90° C. The dried part was then heated in an air-purged oven at 280° C. for 2 hours to remove the HPMC and then heated to a sintering temperature of 900° C. at a rate of 10° C. per minute holding for 30 minutes to sinter the porous tissue scaffold. The porosity of this sample was measured to be 48.0%.

In a fourth exemplary embodiment a porous tissue scaffold is formed from borate glass by mixing 22.5 grams of 13-93B3 borate glass fiber having a diameter of 300 nm and chopped to a length of approximately 100 µm with 5 grams HPMC as the binder with 5 grams PMMA with a particle size of about 200 µm as the first pore former having an ignition temperature of approximately 350° C. and 2.5 grams graphite powder with a particle size ranging between 70-140 μm as the second pore former having an ignition temperature of approximately 600° C. and approximately 13 ml deionized water, adjusted as necessary to provide a plastically formable mixture. The mixture was formed into a 10 mm diameter rod and dried in a convection oven at 90° C. The dried part was then heated in an air-purged oven at 280° C. for 2 hours to remove the HPMC and then heated to a sintering temperature of 650° C. at a rate of 10° C. per minute holding for 30 minutes to sinter the porous tissue scaffold.

The present invention has been herein described in detail with respect to certain illustrative and specific embodiments thereof, and it should not be considered limited to such, as numerous modifications are possible without departing from the spirit and scope of the appended claims.

What is claimed is:

1. A method of fabricating a porous tissue scaffold comprising:
    providing a bioactive material, the bioactive material having a discrete size distribution;
    providing a plurality of pore formers including at least a first pore former material and a second pore former material, the first pore former material having an ignition temperature that is less than an ignition temperature of the second pore former material, wherein at least one of the first pore former and the second pore former is PMMA;
    providing a binder and a liquid;
    mixing the bioactive material with the first pore former, the second pore former, the binder and the liquid to provide a green mixture;
    forming the green mixture into an object;
    heating the object to remove the fluid and the binder;
    heating the object to a temperature that is at least the ignition temperature of the first pore former material to initiate a combustion of the first pore former;
    heating the object to a temperature that is at least the ignition temperature of the second pore former using the combustion of the first pore former to initiate a combustion of the second pore former; and
    bonding the bioactive material in the object using the combustion of the second pore former to provide the porous tissue scaffold.

2. A method of fabricating a porous tissue scaffold comprising:
    providing a bioactive material, the bioactive material having a discrete size distribution;
    providing a plurality of pore formers including at least a first pore former material and a second pore former material, the first pore former material having an ignition temperature that is less than an ignition temperature of the second pore former material, wherein at least one of the first pore former and the second pore former has a particle size of about 0.1 to about 100 times of a mode of the discrete size distribution of the bioactive material;
    providing a binder and a liquid;
    mixing the bioactive material with the first pore former, the second pore former, the binder and the liquid to provide a green mixture;
    forming the green mixture into an object;
    heating the object to remove the fluid and the binder;
    heating the object to a temperature that is at least the ignition temperature of the first pore former material to initiate a combustion of the first pore former;
    heating the object to a temperature that is at least the ignition temperature of the second pore former using the combustion of the first pore former to initiate a combustion of the second pore former; and
    bonding the bioactive material in the object using the combustion of the second pore former to provide the porous tissue scaffold.

3. A method of fabricating a porous tissue scaffold comprising:
    providing a bioactive material, the bioactive material having a discrete size distribution;
    providing a plurality of pore formers including at least a first pore former material and a second pore former material, the first pore former material having an ignition temperature that is less than an ignition temperature of the second pore former material, wherein the ignition temperature of the first pore former is about 350° C. and the ignition temperature of the second pore former is about 650° C.;
    providing a binder and a liquid;
    mixing the bioactive material with the first pore former, the second pore former, the binder and the liquid to provide a green mixture;
    forming the green mixture into an object;
    heating the object to remove the fluid and the binder;
    heating the object to a temperature that is at least the ignition temperature of the first pore former material to initiate a combustion of the first pore former;
    heating the object to a temperature that is at least the ignition temperature of the second pore former using the combustion of the first pore former to initiate a combustion of the second pore former; and
    bonding the bioactive material in the object using the combustion of the second pore former to provide the porous tissue scaffold.

4. A method of fabricating a porous tissue scaffold comprising:
    providing a bioactive glass, the bioactive glass having a discrete size distribution;
    providing a first pore former material and a second pore former material, the first pore former material having an ignition temperature that is less than an ignition temperature of the second pore former material wherein at least one of the first pore former and the second pore former is PMMA;
    providing a binder and a liquid;
    mixing the bioactive glass with the first pore former, the second pore former, the binder and the liquid to provide a green mixture;
    forming the green mixture into an object;
    heating the object to remove the fluid and the binder;
    heating the object to a temperature that is at least the ignition temperature of the first pore former material to initiate a combustion of the first pore former;
    heating the object to a temperature that is at least the ignition temperature of the second pore former using the combustion of the first pore former to initiate a combustion of the second pore former; and
    sintering the bioactive glass using the combustion of the second pore former to form the porous tissue scaffold.

5. A method of fabricating a porous tissue scaffold comprising:
    providing a bioactive glass, the bioactive glass having a discrete size distribution;
    providing a first pore former material and a second pore former material, the first pore former material having an ignition temperature that is less than an ignition temperature of the second pore former material wherein at least one of the first pore former and the second pore former has a particle size of about 0.1 to about 100 times of a mode of the discrete size distribution of the bioactive material;
providing a binder and a liquid;
mixing the bioactive glass with the first pore former, the second pore former, the binder and the liquid to provide a green mixture;
forming the green mixture into an object;
heating the object to remove the fluid and the binder;
heating the object to a temperature that is at least the ignition temperature of the first pore former material to initiate a combustion of the first pore former;
heating the object to a temperature that is at least the ignition temperature of the second pore former using the combustion of the first pore former to initiate a combustion of the second pore former; and
sintering the bioactive glass using the combustion of the second pore former to form the porous tissue scaffold.

6. A method of fabricating a porous tissue scaffold comprising:
providing a bioactive glass, the bioactive glass having a discrete size distribution;
providing a first pore former material and a second pore former material, the first pore former material having an ignition temperature that is less than an ignition temperature of the second pore former material wherein the ignition temperature of the first pore former is about 350° C. and the ignition temperature of the second pore former is about 650° C.;
providing a binder and a liquid;
mixing the bioactive glass with the first pore former, the second pore former, the binder and the liquid to provide a green mixture;
forming the green mixture into an object;
heating the object to remove the fluid and the binder;
heating the object to a temperature that is at least the ignition temperature of the first pore former material to initiate a combustion of the first pore former;
heating the object to a temperature that is at least the ignition temperature of the second pore former using the combustion of the first pore former to initiate a combustion of the second pore former; and
sintering the bioactive glass using the combustion of the second pore former to form the porous tissue scaffold.

* * * * *